United States Patent [19]

Mizutani et al.

[11] Patent Number: 5,027,646
[45] Date of Patent: Jul. 2, 1991

[54] METHOD OF EVALUATING AIR-FUEL RATIO SENSOR AND APPARATUS THEREFOR

[75] Inventors: Yoshihiko Mizutani, Nagoya; Noriyuki Ina, Okazaki; Toshio Yamada, Nagoya, all of Japan

[73] Assignee: NGK Insulators, Ltd., Japan

[21] Appl. No.: 546,765

[22] Filed: Jul. 2, 1990

[30] Foreign Application Priority Data

Jul. 1, 1989 [JP] Japan ................... 1-168314

[51] Int. Cl.$^5$ .......................... G01M 19/00
[52] U.S. Cl. .................... 73/118.1; 436/160
[58] Field of Search ............. 73/118.1, 23.32, 23.31; 436/160

[56] References Cited

U.S. PATENT DOCUMENTS 4,878,380 11/1989 Goodman ................... 73/118.1
4,878,381 11/1989 Moser et al. ................ 73/118.1

FOREIGN PATENT DOCUMENTS 0071474 7/1982 European Pat. Off. .
0273765 12/1987 European Pat. Off. .
57-208441 12/1982 Japan .
57-208442 12/1982 Japan .
57-208443 12/1982 Japan .
63-314450 12/1988 Japan .

Primary Examiner—Jerry W. Myracle
Attorney, Agent, or Firm—Parkhurst, Wendel & Rossi

[57] ABSTRACT

A method of evaluating properties of an oxygen sensor used for detecting air-fuel ratio of exhaust gas from internal combustion engine comprises steps of preparing a burnt gas having a predetermined excess air ratio, supplying additional oxidation gas and/or reduction gas into the burnt gas, and detecting an output from the sensor exposed to the mixed gas flow. The supply amount of the additional gas is increased and decreased with a frequency of at least 10 Hz, and a ratio of a supply increasing period to a supply decreasing period is changed to change the supply amount of the additional gas, so that an excess air ratio λ can be controlled similarly to exhaust gas from an actual engine.

6 Claims, 12 Drawing Sheets

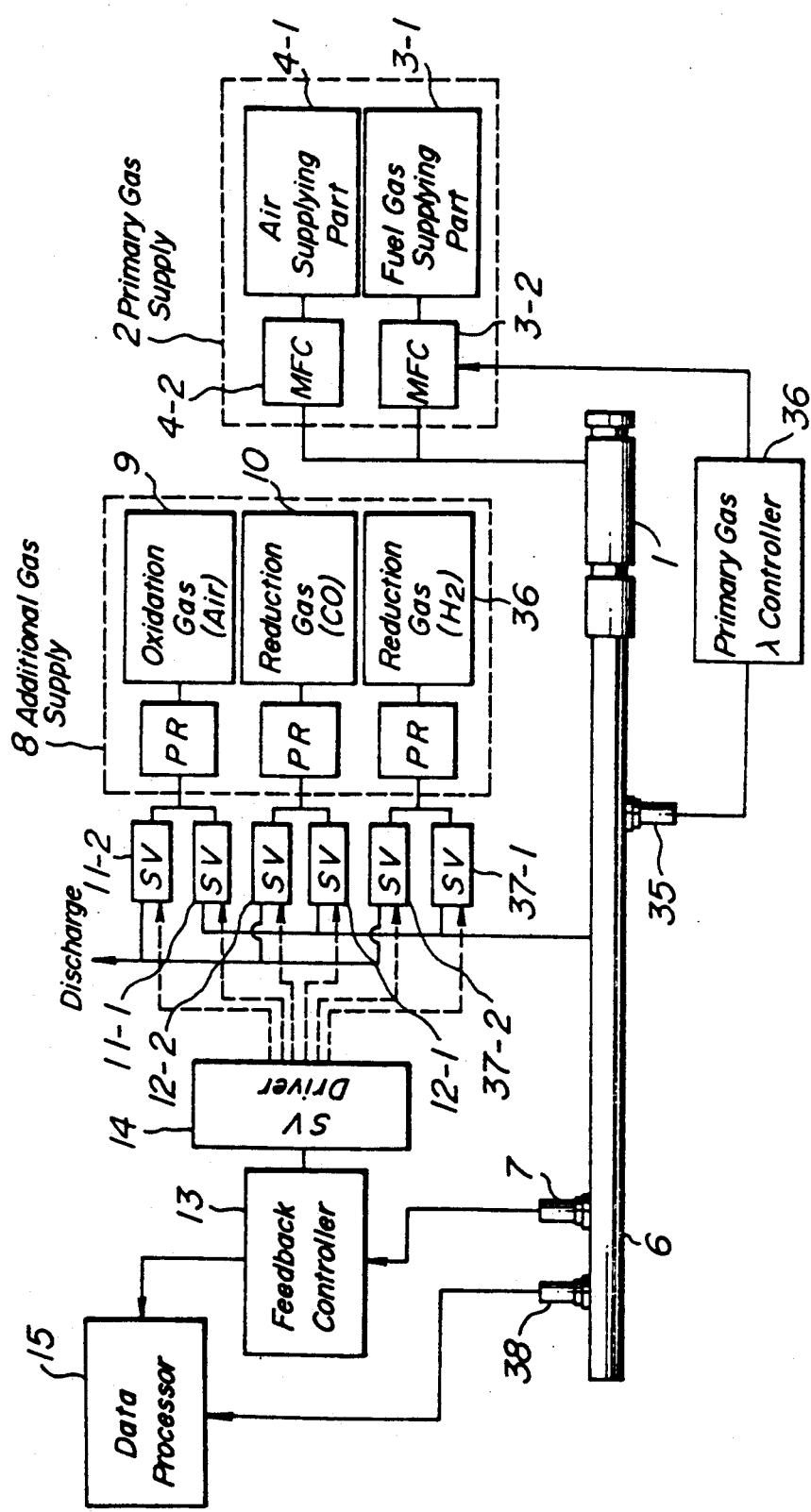
FIG._4

FIG_5
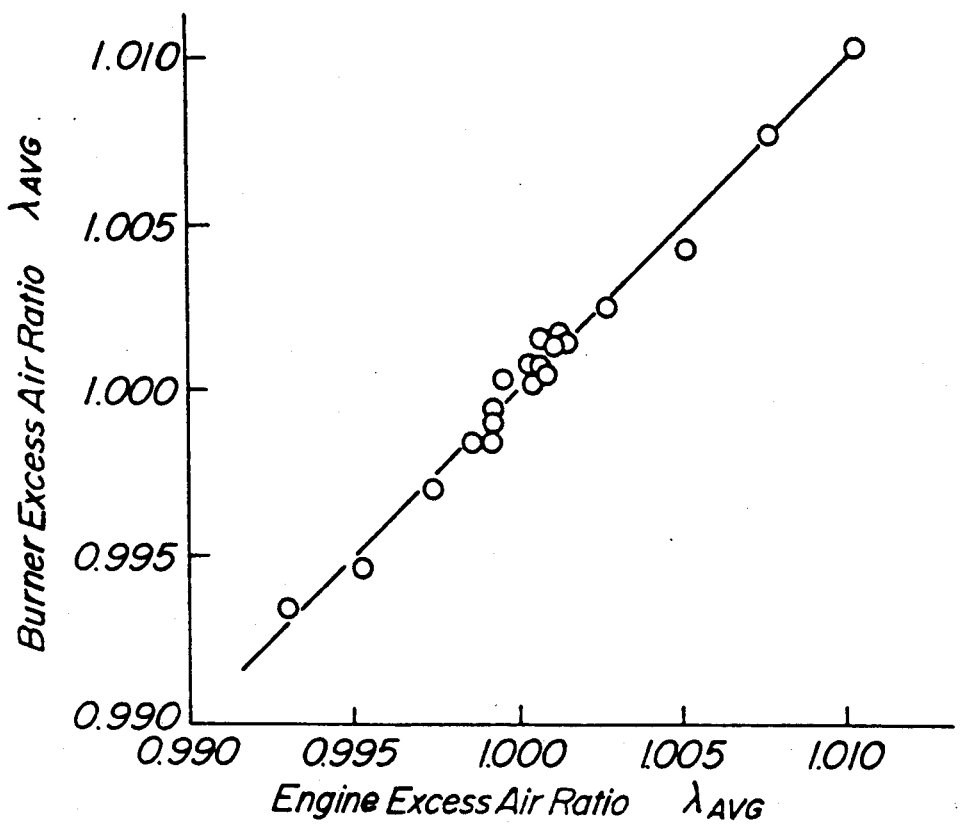
FIG_6
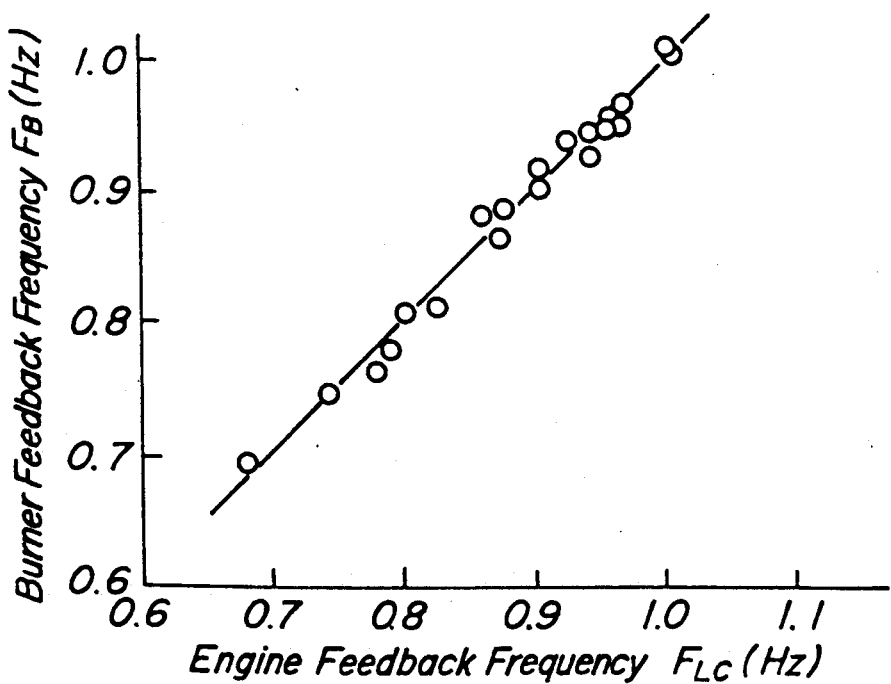

FIG_7
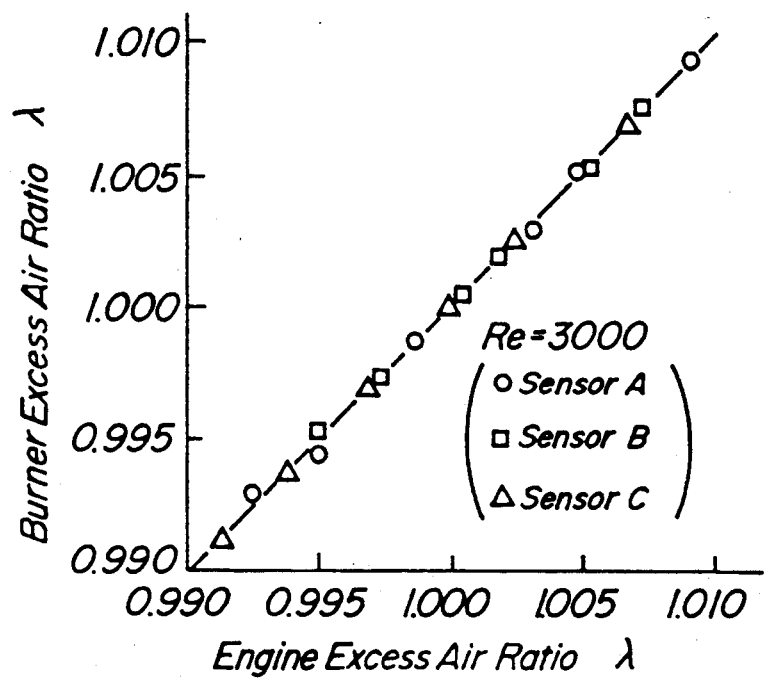
FIG_8
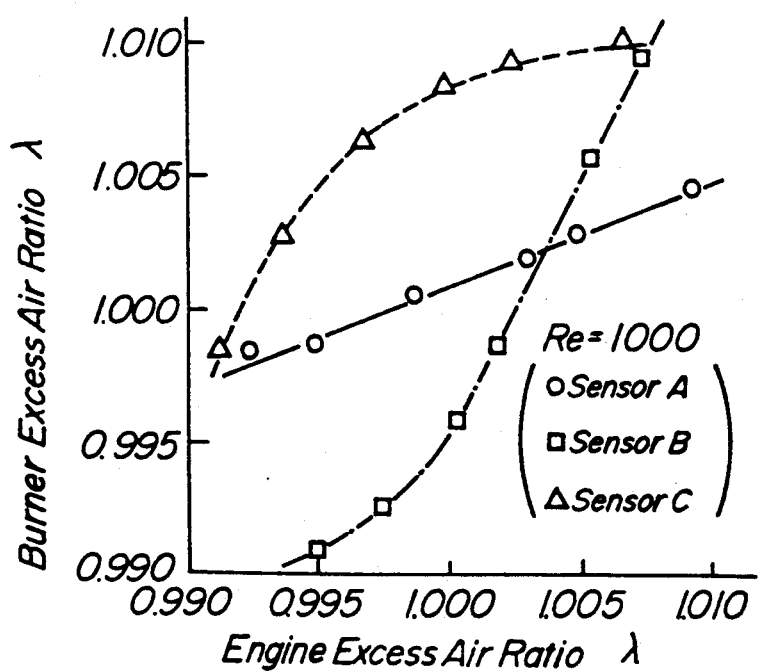

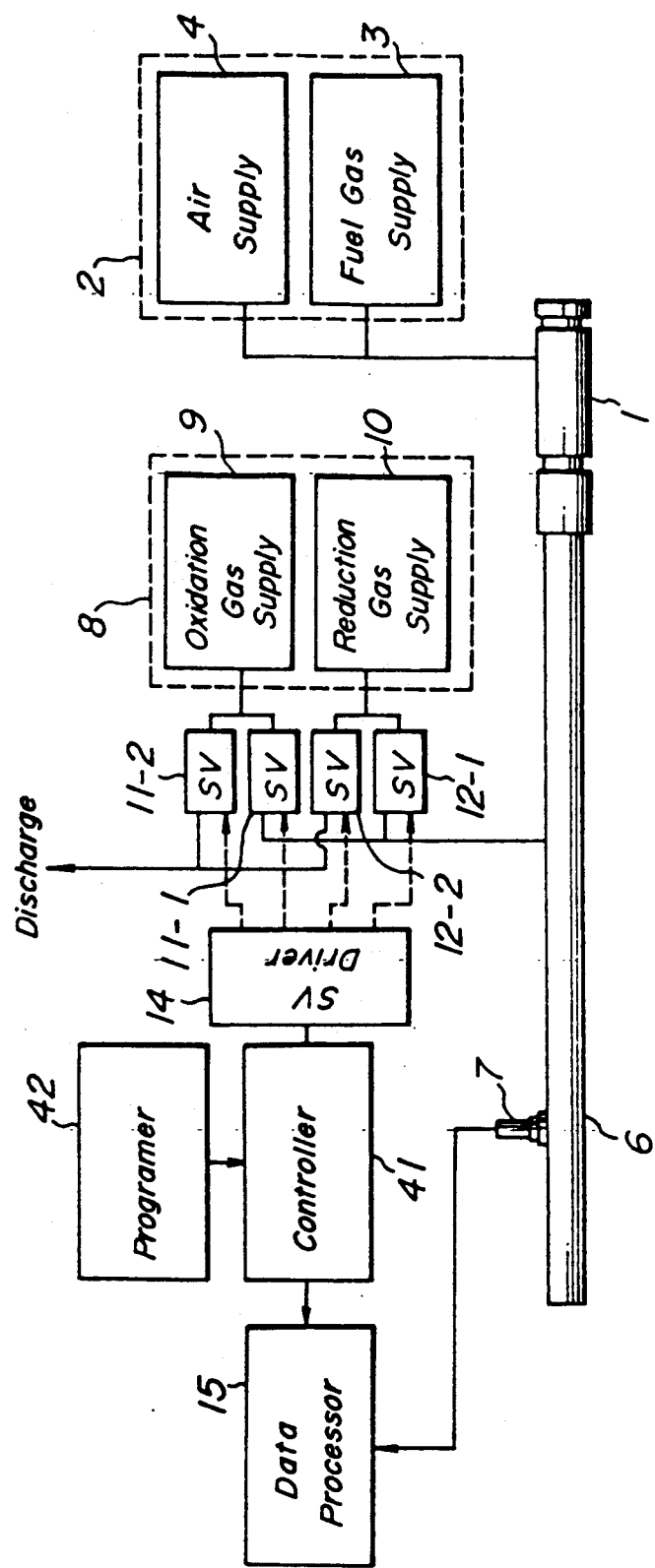

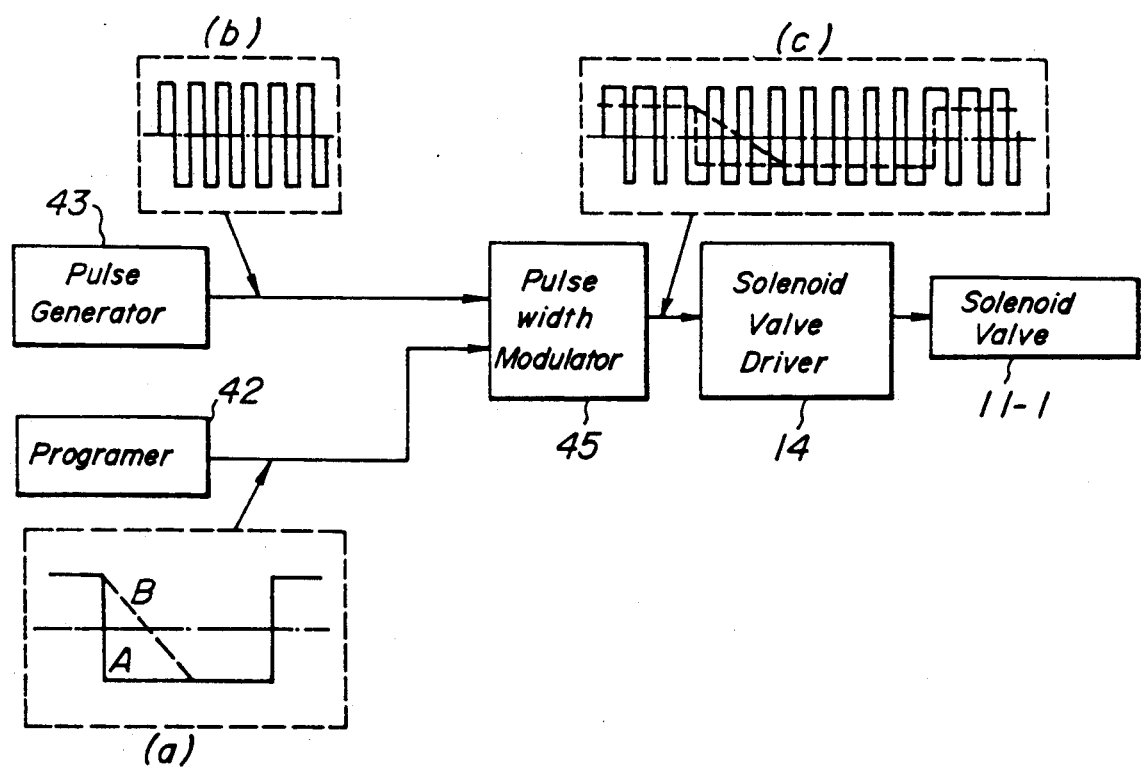
FIG_12

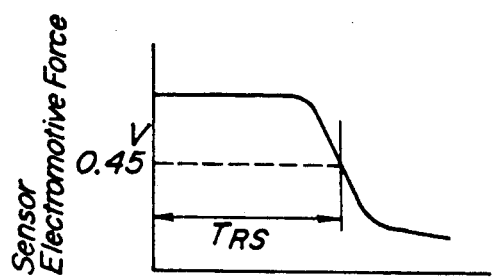
FIG_13a
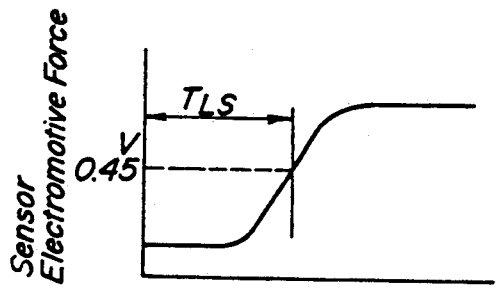
FIG_13b

FIG_13c
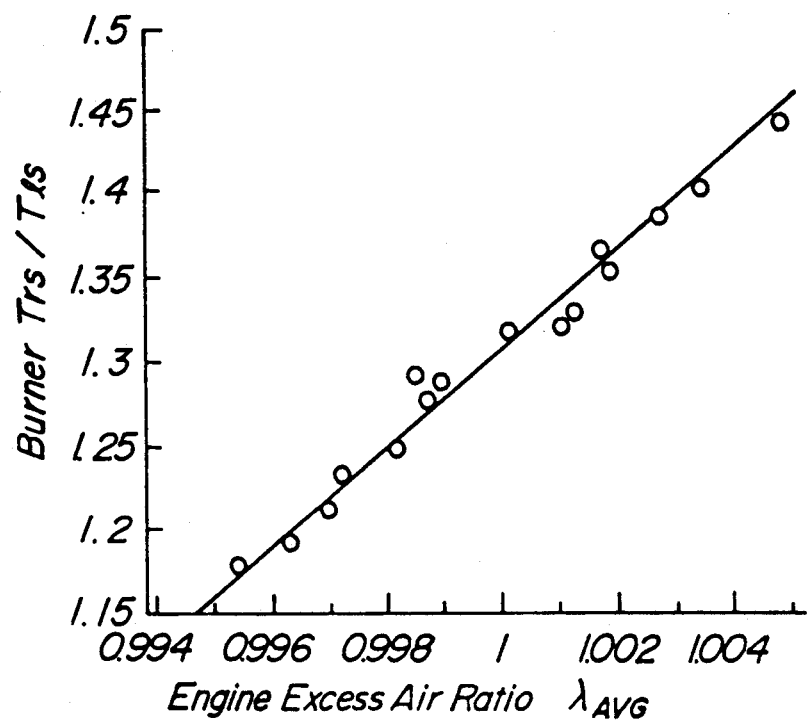
FIG_13d
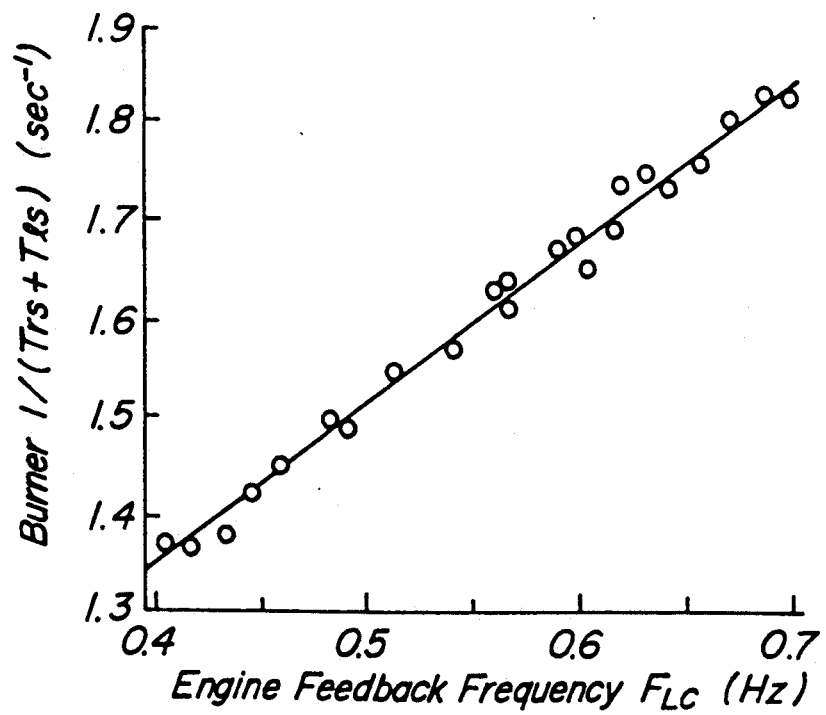

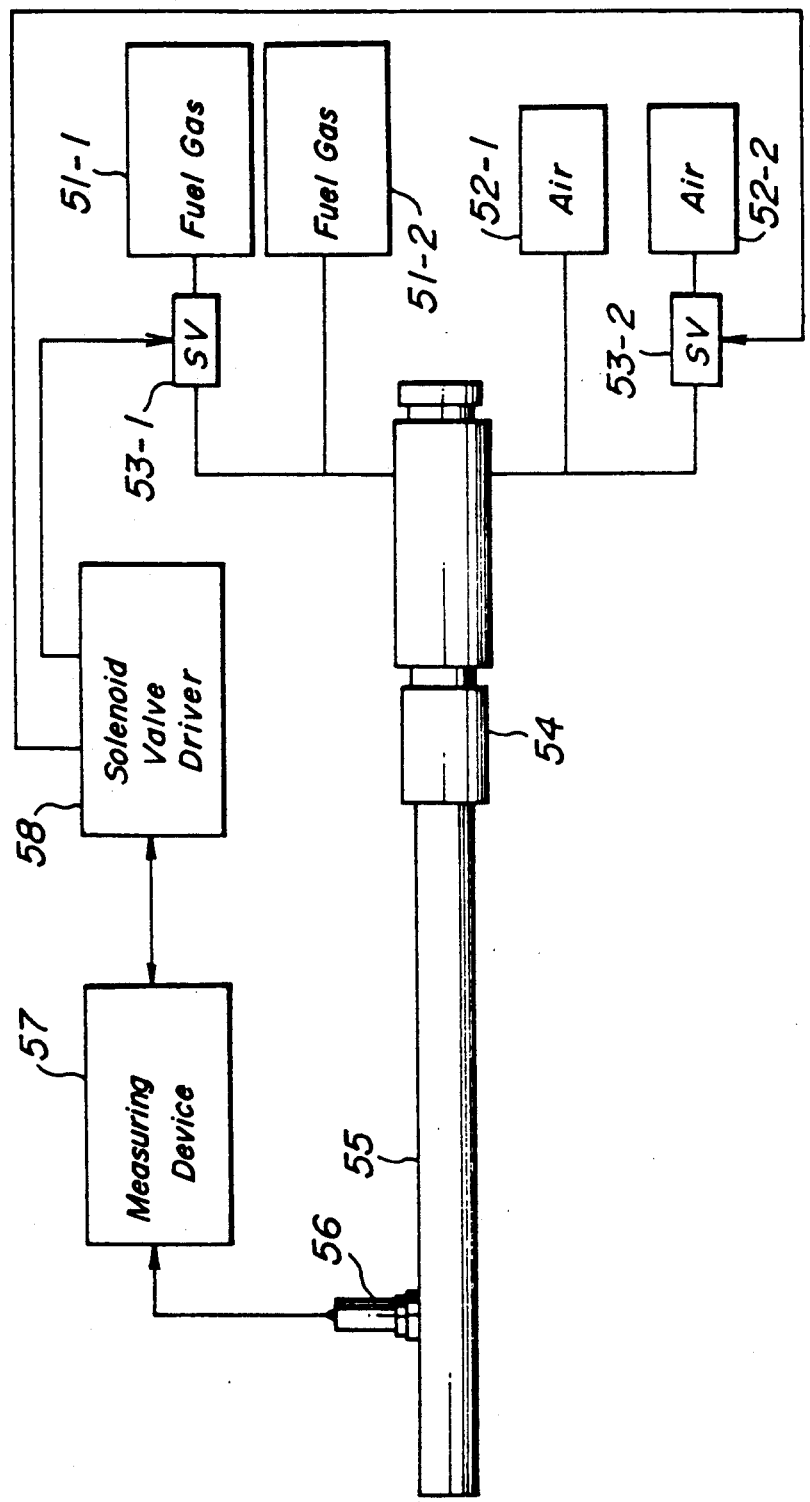

METHOD OF EVALUATING AIR-FUEL RATIO SENSOR AND APPARATUS THEREFOR

BACKGROUND OF THE INVENTION

1. Field of the Invention

The present invention relates to a method of evaluating performance of air-fuel ratio sensors and more particularly, to a method of measuring properties of oxygen sensors consisting of a solid electrolyte used for detecting air-fuel ratio of exhaust gas from internal combustion engines and an apparatus for effecting the evaluating method.

2. Related Art Statement

It is desirable that the evaluation of properties of an oxygen sensor which is used in the exhaust gas of an the internal combustion engine in motor vehicles is effected by actually mounting the oxygen sensor to be measured on the internal combustion engine. However, when the measurements are practically effected with the oxygen sensors actually mounted on the internal combustion engines, the results of measurements vary depending on the kind of engine, control systems, sensor set positions, running conditions, and circumferential conditions (temperature, humidity, pressure). Furthermore, there are problems of stability and economics of measurement since a lot of time and steps are required for measuring the properties of the sensors. Therefore, the measurement of properties can not be practically effected on the actual engine.

Hitherto, there have been used two kinds of measuring methods, one of which is a model gas method in which various kinds of gas supplied from bombs is used to prepare a test gas mixture having a composition as similar as possible to the exhaust gas. The sensor and the test gas mixture are electrically heated under a control. Another method is a combustion gas method in which a fuel gas such as propane, city gas or the like is burnt, the burnt gas being used to measure the properties of the oxygen sensor to be measured.

Among the above mentioned measuring methods, the model gas method has excellent on strictness and stability of measuring conditions, but is mainly used in the laboratory field, since it is expensive and the treating capacity is limited. Therefore, the model gas method is not practical for measuring the performance of a number of sensors. On the other hand, the combustion, method using a gas burner is economical and practical and has a high treating capacity for measuring the performance of a number of sensors, but it can not satisfactorily represent the performance measured on the actual engine.

An example of an apparatus adapted for carrying out the conventional combustion gas method is illustrated in FIG. 14, which is known in a thesis "Characteristics of $ZrO_2$-Type Oxygen Sensors for Automotive Applications" presented by C. T. Young and J. D. Bode at a society in Detroit, Feb. 26–Mar. 2, 1979 as SAE Technical Paper Series No. 790143.

Referring to FIG. 14, fuel gas and air are supplied from fuel gas supplies 51-1 and 51-2 and air supplies 52-1 and 52-2 via gas flow adjusting solenoid valves 53-1 and 53-2, respectively, to a gas burner 54 to mix the fuel gas with air and then burn the gas mixture. The burnt gas from the gas burner is supplied into a cylindrical port 55 which is provided with an oxygen sensor 56 to be measured. The measured data from the oxygen sensor 56 is processed in a measuring device 57 which outputs signals to control a solenoid valve actuator 58.

According to the above arrangement, burnt gas can be obtained simply by burning the gas mixture in the gas burner 54. Thus, a lot of burnt gas can be supplied in a simple manner. The composition of the burnt gas, however, can only be controlled by changing the air-fuel ratio of fuel gas and air supplied to the gas burner 54.

Therefore, there are disadvantages that the burnt gas can not be perfectly imitated to the exhaust gas from the actual internal combustion engine since the gas mixture is burnt under a complete combustion condition and the amount of unburned gas is slight. Furthermore, in the aforementioned apparatus, only a detecting portion of the oxygen sensor 56 is exposed to a burnt gas flow in the cylindrical port 55 so that the burnt gas flow can not sufficiently contact the detecting portion of the oxygen sensor 56 for a short time and consequently, the properties of the sensor can not be accurately evaluated.

SUMMARY OF THE INVENTION

It is an object of the present invention to overcome the aforementioned problems and to provide a method of evaluating properties of sensors in an improved correlation with values measured on actual engines in a manner as simple as the combustion gas method using the gas burner, and to provide an apparatus therefor.

According to the first aspect of the present invention, a method of evaluating properties of an oxygen sensor used for detecting the air-fuel ratio of exhaust gas from an internal combustion engine comprises the steps of preparing a burnt gas having a predetermined excess air ratio, mixing the burnt gas with additional oxidation and/or reduction gas, exposing the sensor to the mixed gas flow, and detecting an output from the sensor. A supply of the additional gas is increased and decreased with a frequency of at least 10 Hz and a ratio of a supply increasing period to a supply decreasing period is changed to changed the supply amount of the additional gas. The ratio of the supply increasing period to the supply decreasing period is changed with a frequency lower than the gas supply amount changing frequency or stepwise.

According to the second aspect of the present invention, an apparatus for evaluating properties of an oxygen sensor which is used for detecting the air-fuel ratio of exhaust gas from an internal combustion engine, comprises a burnt gas producing part for producing a burnt gas having a predetermined excess air ratio by burning a combustible gas mixture of fuel gas and combustion air, a measuring part for mounting the oxygen sensor to be measured, a connecting part for guiding a flow of the burnt gas to the oxygen sensor, an additional gas introducing part for introducing additional oxidation and/or reduction gas into the burnt gas flow, a gas flow rate controlling part for controlling a flow rate of the additional gas introduced into the burnt gas in a manner of high speed pulse width control, and a pulse width controlling part for controlling pulse width of the additional gas supply in cycle or stepwise.

In the arrangement mentioned above, the supply amount of the additional gas is increased and decreased in a cycle or stepwise with a frequency of at least 10 Hz and a ratio of supply increasing period to supply decreasing period is controlled to change the supply amount of the additional gas. Accordingly, the supply amount of the additional gas can be changed with high frequency of at least ten times per second and therefor the excess air ratio (expressed by λ hereinafter) can be finely controlled.

Consequently, it is possible to evaluate the properties of a sensor with values approximate to those measured on the actual engine.

The excess air ratio (λ) means a value of an amount of air supplied for burning an amount of fuel gas divided by an amount of air required for completely burning the amount of fuel gas. When λ=1, the fuel gas is completely burnt. When λ is smaller than one, the air supply amount is in a shortage condition (hereinafter called rich) and when λ is larger than one, the air supply amount is in an excess condition (hereinafter called lean).

The frequency of increasing and decreasing the supply amount of the additional gas is set to at least 10 Hz, since an electronic fuel injection engine has the same minimum fuel injection frequency. That is, most of the electronic fuel injection engines effect one fuel injection per one revolution and then the fuel injection frequency in a range of normal number of revolutions of 650 rpm~6000 rpm is in a range of 10.8 Hz~100 Hz.

Moreover, since the frequency of increasing and decreasing supply amount of the additional gas is set to at least 10 Hz, the additional oxidation gas and reduction gas can be repeatedly increased and decreased with a frequency of at least ten times per second. After the burnt gas is mixed with the additional gases, the value of λ of the mixed gas is compensated. Accordingly, even if the flow rate of the additional gases is large, the variation range of λ can be reduced and the measuring λ range can be accurately set in the proximity of the λ of the engine exhaust gas. Consequently, the properties of the oxygen sensors can be measured in a high correlation with values measured on the actual engine.

BRIEF DESCRIPTION OF THE DRAWINGS

The present invention will be described in more detail by reference to embodiments in connection with the accompanying drawings, in which:

FIG. 4 is a block diagram showing other embodiment of the apparatus of the present invention;

FIG. 5 is a graph showing a relationship between excess air ratio of burnt gas from a burner of the present invention and excess air ratio of exhaust gas from an actual engine;

FIG. 6 is a graph showing a relationship between feedback frequencies of the present invention and actual engine;

FIGS. 7 and 8 are graph each showing a relationship between excess air ratio of burnt gas from a burner of the present invention and excess air ratio of exhaust gas from an actual engine when Reynolds number at a sensor measuring part is changed;

FIG. 11 is a block diagram of the third embodiment of the apparatus of the invention;

FIG. 12 is a block diagram showing another embodiment of a controller of the present invention together with wave shapes of output signals from respective parts;

FIGS. 13a and 13b are graphs showing variation of sensor electromotive force according to the invention, respectively;

FIGS. 13c and 13d are graphs each showing a relationship between values measured in an actual engine and results evaluated according to the present invention; and FIG. 14 is a block diagram showing a prior art apparatus for evaluating properties of the sensor.

DETAILED EXPLANATION OF THE PREFERRED EMBODIMENTS

Figure 1:
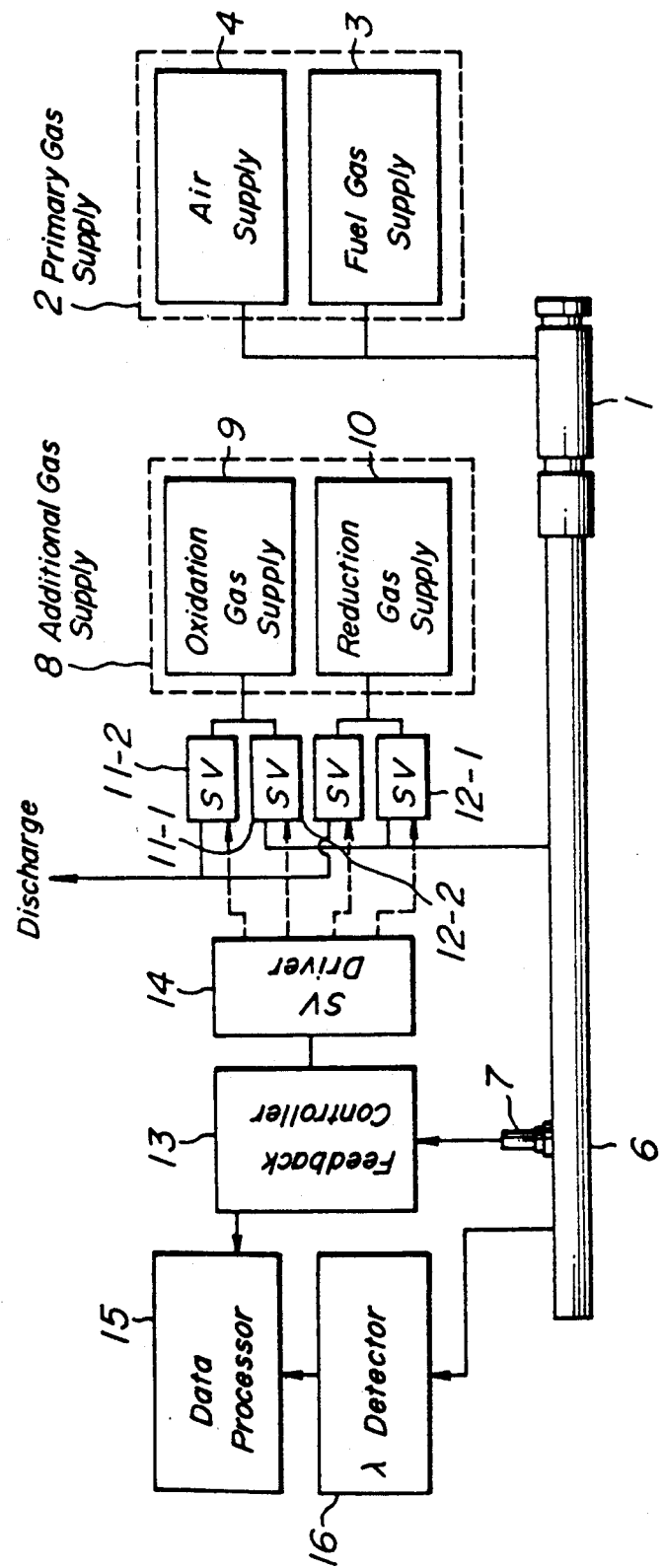
FIG. 1 is a block diagram of an embodiment of the apparatus for evaluating the air-fuel ratio sensor according to the present invention.

FIG. 1 shows an embodiment of the apparatus for evaluating air-fuel ratio sensors according to the present invention. Referring to FIG. 1, fuel gas and air as a combustion base gas are supplied to a gas burner 1 from a fuel gas supply 3 and an air supply 4 of a primary gas supply 2 and burnt in the gas burner 1 to produced burnt gas having a predetermined air-fuel ratio. The burnt gas flows from the gas burner to a sensor to be measured within a cylindrical port 6. A controlled amount of oxidation gas or reduction gas is supplied into the cylindrical port 6 between the gas burner 1 and sensor 7 from an oxidation gas supply 9 or a reduction gas supply 10 of an additional gas supply by controlling a solenoid valve 11-1 or 12-1. Moreover, in this embodiment, relief valves 11-2 and 12-2 are connected to the oxidation gas supply 9 and the reduction gas supply 10 in parallel to the solenoid valves 11-1 and 12-1, respectively, to increase the flow of gas when the flow through the solenoid valves 11-1 and 12-1 decreases, and to decrease when the flow through the solenoid valves 11-1 and 12-1 increases to thereby maintain a pressure in the line a constant by relief valves when the additional gas supply varies.

Furthermore, the sensor 7 outputs detected signals to a feedback controller 13 to process the signals. The controller 13 outputs control signals to a solenoid valve driver 14 to control solenoid valves 11-1, 11-2, 12-1 and 12-2 to thereby prepare a gas mixture having a predetermined composition. At the same time, the sensor 7 also supply output signals to a data processor 15 to process the signals together with results measured by a λ detector 16 which detects an atmosphere at the tip end of the cylindrical port 6 to thereby evaluate properties of the sensor to be measured.

It is noted in the above mentioned apparatus that the gas burner 1 and the primary gas supply 2 constitute the burnt gas producing part, a portion of the cylindrical port 6 constitutes the measuring part, a portion of the cylindrical port 6 constitutes the connecting part, the additional gas supply 8 and the solenoid valve 11-1, 12-1 constitute the additional gas introducing part, a portion of the feedback controller 13 and the electromagnetic driver 14 constitute the gas flow rate controlling part, and a portion of the feedback controller 13 constitutes the pulse width controlling part.

Figure 2:
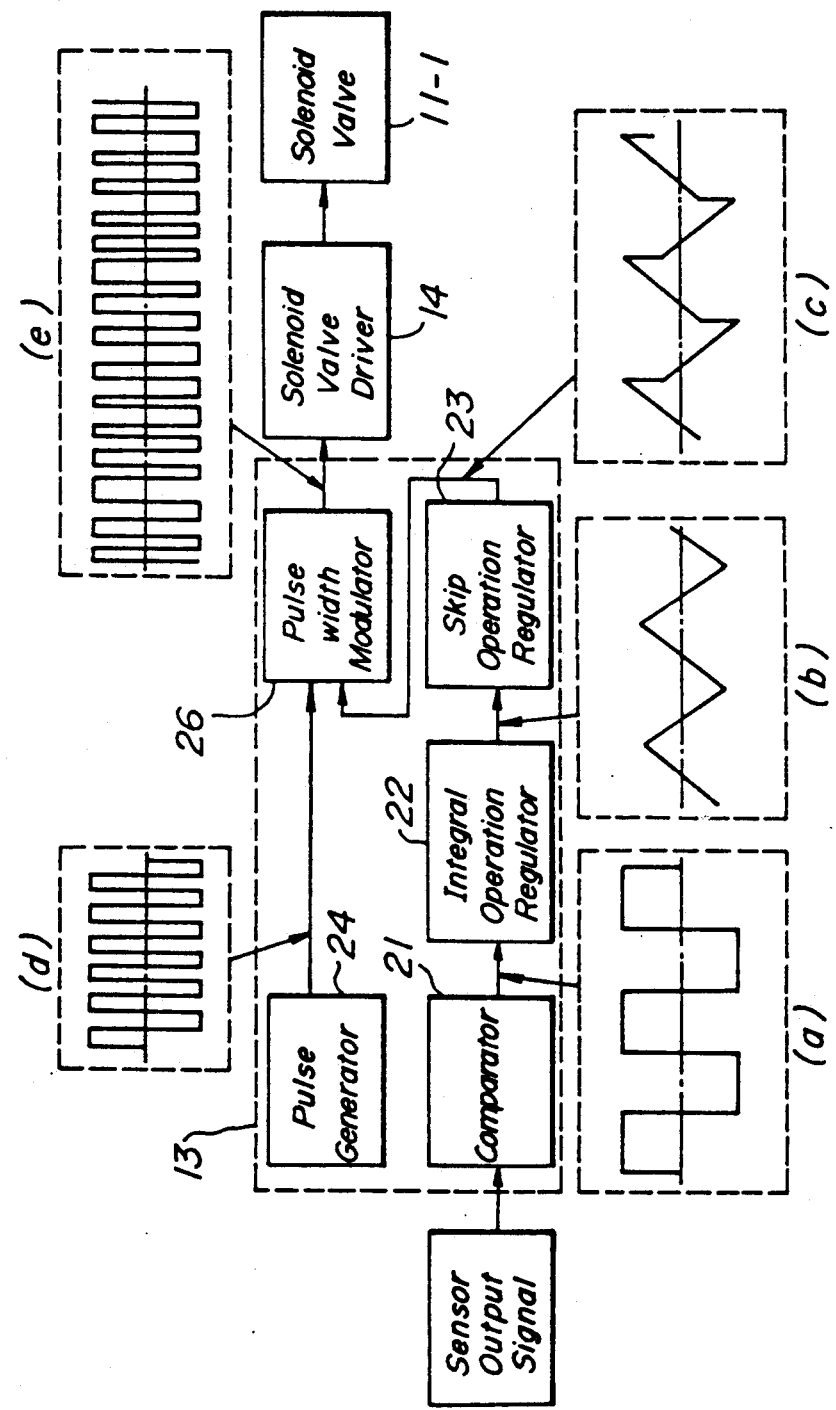
FIG. 2 is a block diagram showing an embodiment of a feedback controller together with wave forms of output signals from respective parts.

FIG. 2 is a block diagram showing an embodiment of a feedback controller together with waveforms of signals output from respective parts. Referring to FIG. 2, the sensor 7 outputs signals to a comparator 21. When the sensor to be measured is the normal $ZrO_2$ type solid electrolyte oxygen sensor, its output voltage in lean atmosphere is at most 200 mV (hereinafter, termed lean voltage) and the output voltage in rich atmosphere is at least 700 mV (hereinafter, termed rich voltage). First, an intermediate voltage between the rich voltage and the lean voltage (for example 450 mV) is used as the reference voltage to transduce the sensor output voltage in the comparator 21 to a pulse waveform (a) as shown in the drawing. Secondly, the pulse signal is supplied to an integral operation regulator 22 to transduce the pulse waveform to a sawtooth waveform (b), and thirdly the signal is supplied to a skip operation regulator 23 to transduce the waveform (b) to another waveform (c) as shown in the drawing. At the same time, a pulse generator 24 outputs a pulse signal having a constant frequency of at least 10 Hz. A pulse width modulator 26 modulates the pulse width of a signal (d) together with the signal (c) which has been skip transduced to output a feedback controlling pulse signal (e) which has the same frequency and a different duty ratio. This feedback controlling pulse signal is supplied to the solenoid valve driver 14 to control the supply amount of the additional gas supplied to the cylindrical port 6 in such a manner that the flow rate of the gas is increased when the pulse signal is positive and the flow rate is decreased when the pulse signal is negative.

In the control operation mentioned above, the solenoid valves 11-1 and 12-1 for discontinuously supplying the oxidation gas and reduction gas, respectively, operate in such a manner that when the oxidation gas is increased, the reduction gas is decreased and when the oxidation gas is decreased, the reduction gas is increased. It is preferable to control the additional gases to supply into the cylindrical port through a supply port since the time of increasing and decreasing the additional gases is fixed and consequently, any time lag of the peak λ value and the change between increasing and decreasing periods is removed. Moreover, the feedback control signal is added with an integral operation and a skip operation each of which can be voluntarily set. Accordingly, the integral operation and the skip operation can be regulated to easily match to feedback properties of various engines.

Figure 3:
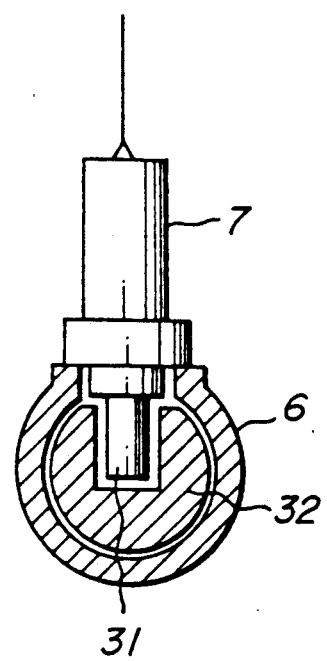
FIG. 3 is a partially sectional view of sensor measuring part in the apparatus shown in FIG. 1.

FIG. 3 is a partially sectional view of the sensor measuring part in the apparatus shown in FIG. 1. Referring to FIG. 3, a throttle member 32 is arranged around a detecting portion 31 of the sensor 7 in the cylindrical port 6 to locally limit the gas flow passage of the cylindrical port at the sensor mounting portion. The burnt gas from the burnt gas producing part for use in measurement has a flow rate and pressure lower than those of exhaust gas discharged from the engine and difference of responsibility depending on the configuration of the detecting portion 31 of the sensor 7. The tip vent mechanism differ from the engine exhaust gas measuring value. Therefore, the sectional area of the gas flow passage at the sensor mount position is limited to increase the flow resistance around the detecting portion of the sensor to thereby increase the substituting speed of the test gas in the sensor. As a result, a relationship of responsibility similar to the engine can be obtained and the gas flow rate to be required can be economically reduced.

FIG. 4 is a block diagram showing another embodiment of the apparatus for evaluating an air-fuel ratio sensor according to the present invention. In the embodiment shown in FIG. 4, portions corresponding to those shown in FIG. 1 are designated by the same reference numerals and their detailed descriptions are omitted.

FIG. 4 is different from the embodiment shown in FIG. 1 in that the air supply 4 consists of an air supply part 4-1 and a mass flow controller 4-2 (hereinafter, call MFC for short) and the fuel gas supply 3 consists of a fuel gas supplying part 3-1 and MFC 3-2. Moreover, a large range air-fuel ratio sensor 31 is arranged at a downflow of the gas burner 1. The sensor 35 outputs to a primary gas λ controller 36 which controls the MFC 3-2. Consequently, the λ can be accurately maintained at a constant value. The additional gas supply 8 includes an oxidation gas supply 9 for supplying air, a reduction gas supply 10 for supplying CO gas and further a reduction gas supply 36 for supplying $H_2$ gas. The reduction gas supply 36 also supplies $H_2$ gas through the same supply port together with the air and CO gas under control by the solenoid valves 37-1 and 37-2 to make the burnt gas similar to the exhaust gas. Furthermore, a large range air-fuel ratio sensor 38 is arranged in place of the λ detector 16 to determine the properties of the sensor to be measured. The arrangement of the feedback controller 13 in this embodiment is the same as that shown in FIG. 2.

In the embodiment shown in FIG. 4, the gas burner 1 and the primary gas supply 2 constitute the burnt gas producing part, a portion of the cylindrical port 6 constitutes the measuring part, a portion of the cylindrical port 6 constitutes the connecting part, the additional gas supply 8 and the solenoid valves 11-1, 12-1 and 37-1 constitute the additional gas introducing part, a portion of the feedback controller 13 and the solenoid valve driver 14 constitute the gas flow rate controlling part, and a portion of the feedback controller 13 constitutes the pulse width controlling part.

In the embodiment shown in FIG. 4, the primary gas and the additional gas was supplied at the flow rate shown in Table 1, the frequency of open and close operation of the solenoid valve being 20 Hz. The increasing and decreasing of the additional gas was feedback controlled so as to maintain the measuring sensor at a predetermined voltage (for example 450 mV) and the excess air ratio $\lambda_{AVG}$ and the feedback frequency $F_B$ was measured. On the other hand, the same sensor to be measured was mounted on an actual internal combustion engine. This engine was driven at 1150 rpm and the excess air ratio $\lambda_{AVG}$ and the feedback frequency $F_{LC}$ was measured during feedback controlling by the sensor. FIG. 5 shows a correlation of excess air ratio and FIG. 6 shows a correlation of feedback frequency. It will be seen from the results shown in FIGS. 5 and 6 that the present invention can evaluate the properties of a sensor under substantially the same condition as that of the actual engine.

TABLE 1

|  | Kind of gas | Flow rate (ml/min) | Nature |
| --- | --- | --- | --- |
| Primary gas | Propane | 740 | Neutral gas |
|  | Air | 1730 | (λ = 1) |
| Additional gas | CO | 550 | Reduction gas |
|  | $H_2$ | 870 |  |
|  | Air | 1310 | Oxidation gas |

In order to investigate an influence of Reynolds number Re(=4 mV/ν; m:(sectional area of gas passage at the measuring part)/(circumference length of the cross section of gas passage at the measuring part), V: mean velocity of the test gas at the measuring part, $\nu$: kinematic coefficient of viscosity of measuring gas) of the test gas at a sensor mounting position, the excess air ratio $\lambda_{AvG}$ was determined in each case of using sensors A, B and C each having a detecting portion of different shape. It will be found from results of the test that when the Reynolds number Re is 3000, a high correlation is obtained between the burner excess air ratio and the engine excess air ratio in spite of the kind of the sensors as shown in FIG. 7, but when the Reynolds number Re 1000, the correlation is greatly varies depending on the kind of the sensors, as shown in FIG. 8. It is confirmed from the results that it is preferable to have the Reynolds number Re of at least 2500 of the test gas in the sensor mounting position.

Figure 9:
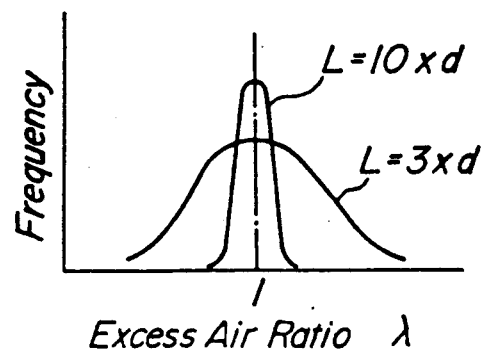
FIG. 9 is a graph showing dispersion of excess air ratio when a position of the sensor at the measuring part is changed.

Moreover, in order to investigate an influence of sensor mounting position, dispersion of the excess air ratio $\lambda$ was determined in each case that a distance L from the additional gas mixing part to a position of the sensor to be measured is 10 times and 3 times of an inner diameter "d" of the cylindrical port 6 shown in FIG. 4. The results of the test are shown in FIG. 9. As will be seen from the graph shown in FIG. 9, the dispersion in the case of L=10d is less than that in the case of L=3d and therefore, a condition similar to the exhaust gas from the actual engine can be provided.

Figure 10:
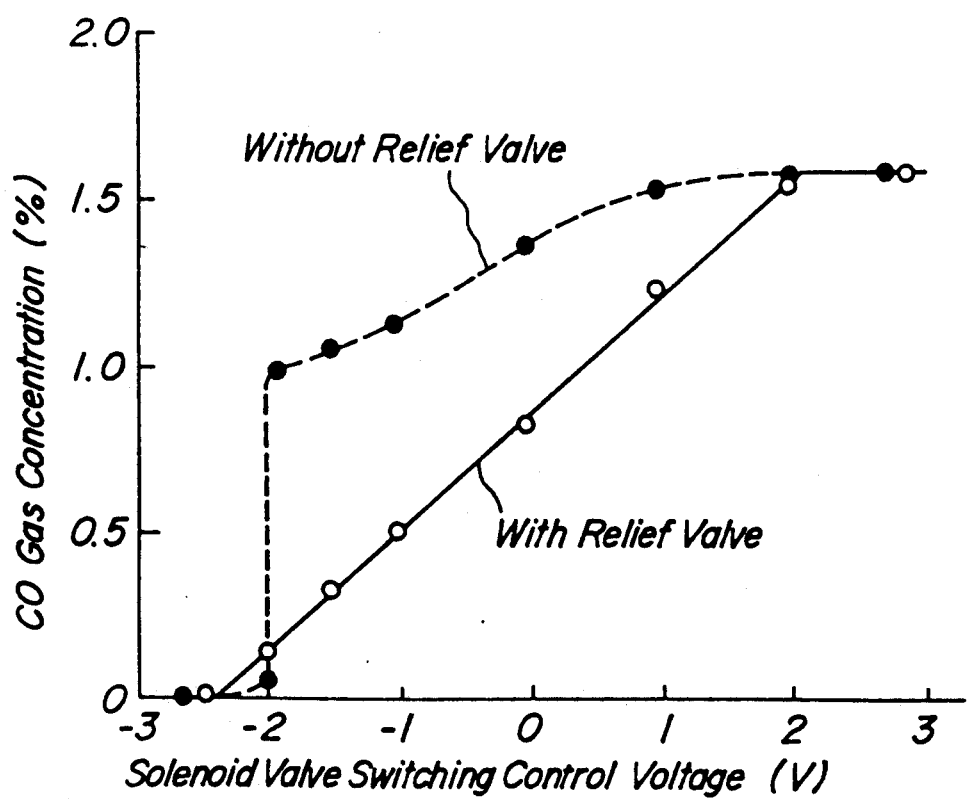
FIG. 10 is a graph showing a relationship between concentration of CO gas and control voltage for opening a solenoid valve in the apparatus with a relief valve and without a relief valve.

In the apparatus shown in FIG. 4, in order to investigate influence of the relief valve, a relationship between a concentration of CO gas solely added to the burnt gas and a solenoid valve switching control voltage was determined and a result as shown in FIG. 10 obtained. It will be seen from the result shown in FIG. 10 that the gas flow rate can be more accurately controlled by providing the relief valve. Similar results were also obtained in the case of addition of other additional gases such as air and $H_2$.

FIG. 11 shows another embodiment of the apparatus for evaluating an air-fuel ratio sensor according to the present invention. This embodiment is adapted for an open loop measurement, but not for feedback control as mentioned above. In the embodiment shown in FIG. 11, portions corresponding to those shown in FIG. 1 are designated by the same reference numerals and their detailed descriptions are omitted. In this embodiment, the sensor 7 to be measured directly supplies output to the data processor 15, and a controller 41 which differs from the feedback controller 41 is provided to cooperate with a programmer 42 so as to control the solenoid valve driver 14 to thereby increase and decrease the supply of the additional gas in high speed.

In the embodiment shown in FIG. 11, the gas burner 1 and the primary gas supply 2 constitute the burnt gas producing part, a portion of the cylindrical part 6 constitutes the connecting part, the additional gas supply 8 and the solenoid valve 11-1~12-1 constitute the additional gas introducing part, a portion of the controller 41 and the solenoid valve driver 14 constitute the gas flow rate controlling part, and a portion of the controller 41 constitutes the pulse width controlling part.

Referring to FIG. 12 showing an embodiment of a controller 41 together with waveforms of signals output from respective parts, firstly a programmer 42 generates a pulse-like signal (a) which is limited to an output of a sensor 7 to be measured. At the same time, a pulse generator 43 generates a pulse signal (b) of a constant frequency of at least 10 Hz, and the pulse-like signal (a) from the programmer 42 and the pulse signal (b) from the pulse generator 43 are supplied to a pulse width modulator 45 to modulate, thereby obtaining a controlling pulse signal (c). At this time, if the pulse-like signal (a) has a waveform (A), the controlling pulse signal (C) changes its duty ratio by every several pulse signals, and if the pulse-like signal from the programmer 42 has a waveform (B) which is changed to coincide with $\lambda$ variation in an engine, the controlling pulse signal (d) has a different duty ratio by every pulse signal.

FIGS. 13a and 13b are graphs showing variation of sensor electromotive force by every switching operation in the above described operation in the above described embodiment. In FIGS. 13a and 13b, $T_{RS}$ and $T_{LS}$ are response times from generation of respective solenoid valve switching signals to the time when the sensor electromotive force becomes a predetermined value (0.45 V in this embodiment). $T_{LS}$ shows the time for varying the sensor electromotive force from the rich side to a predetermined value, and $T_{LS}$ shows the time for varying the sensor electromotive force from the lean side to a predetermined value, respectively. With the use of these $T_{RS}$ and $T_{LS}$, the data processor 15 can evaluate properties of the sensor 7 by using $1/(T_{RS}+T_{LS})$ and $T_{RS}/T_{LS}$ as an index of property evaluation. FIGS. 13c and 13d show an example of the evaluation. It will be understood from FIGS. 13c and 13d that the values measured in an actual engine correlates well with the results evaluated according to the present invention.

In the open type arrangement shown in FIGS. 11~13, a gas control response is better than that of a thermal type mass flow controller, a flow rate can continuously be varied, and even if the supply flow rate is large, small $\lambda$ variation can be set with high precision.

The present invention is not limited to the above embodiments, but can be modified in various modes. For example, in the above embodiments, in view of gas toxicity and economics, three kinds of CO, $H_2$ and air are used as an additional gas, but in order to close to become an exhaust gas combustion, it is possible to obtain a good result by further increasing kinds of additional gases, adding other gas such as NO or $C_3H_6$, $C_3H_8$ and the like represented by $C_nH_{2n}$ and $C_nH_{2n+2}$. Moreover, instead of a wide range air-fuel ratio sensor, a gas analyzer or an oxygen sensor may be used for measuring a duty ratio to thereby evaluate properties of the sensor to be measured.

What is claimed is:

1. A method of evaluating properties of an oxygen sensor used for detecting an air-fuel ratio of exhaust gas from an internal combustion engine, comprising the steps of preparing a burnt gas having a predetermined excess air ratio, supplying additional oxidation gas and/or reduction gas into the burnt gas, and detecting an output from the sensor exposed to a gas flow of the mixed burnt gas and additional gas, wherein a supply amount of the additional gas is increased and decreased with a frequency of at least 10 Hz, and a ratio of a supply increasing period to a supply decreasing period of the additional gas is changed to thereby change a supply amount of the additional gas.

2. The method of claim 1, wherein the ratio of the supply increasing period to the supply decreasing period of the additional gas is changed with a lower frequency than the gas supply amount changing frequency of the additional gas.

3. The method of claim 1, wherein the ratio of the supply increasing period to the supply decreasing period is changed stepwise.

4. The method of claim 1, wherein the supply amount of the additional gas is feedback controlled by an output of the sensor properties of the sensor being evaluated by feedback properties of the feedback control.

5. An apparatus for evaluating properties of an oxygen sensor which is used for detecting an air-fuel ratio of exhaust gas from an internal combustion engine, comprising a burnt gas producing part for producing a burnt gas having a predetermined excess air ratio by burning a combustible gas mixture of fuel gas and combustion air, a measuring part for mounting the oxygen sensor to be measured, a connecting part for guiding a flow of the burnt gas to the measuring part, an additional gas introducing part for introducing additional oxidation gas and/or reduction gas into the burnt gas flow, a gas flow rate controlling part for controlling a flow rate of the additional gas introduced into the burnt gas by high speed pulse width control, and a pulse width controlling part for cyclic or stepwise control of gas supply of the additional gas.

6. The apparatus of claim 5, wherein the gas flow rate controlling part further comprises a relief valve for maintaining a constant pressure therein.

* * * * *